(12) United States Patent
Zhao et al.

(10) Patent No.: US 11,529,437 B2
(45) Date of Patent: Dec. 20, 2022

(54) BIOLOGICAL TISSUE MATRIX MATERIAL, PREPARATION METHOD THEREFOR AND USE THEREOF IN OTOLOGICAL REPAIR MATERIAL (71) Applicant: Beijing Biosis Healing Biological Technology Co., Ltd., Daxing District (CN)

(72) Inventors: Bo Zhao, Beijing (CN); Hongquan Wang, Beijing (CN); Leilei Xia, Beijing (CN); Yanrui Zhao, Beijing (CN); Xuejun Li, Beijing (CN); Jinhui Zhang, Beijing (CN)

(73) Assignee: Beijing Biosis Healing Biological Technology Co., Ltd., Daxing District (CN)

( * ) Notice: Subject to any disclaimer, the term of this patent is extended or adjusted under 35 U.S.C. 154(b) by 622 days.

(21) Appl. No.: 16/486,296

(22) PCT Filed: Apr. 18, 2017

(86) PCT No.: PCT/CN2017/080894
§ 371 (c)(1),
(2) Date: Aug. 15, 2019

(87) PCT Pub. No.: WO2018/157456
PCT Pub. Date: Sep. 7, 2018

(65) Prior Publication Data
US 2020/0230291 A1  Jul. 23, 2020

(30) Foreign Application Priority Data

Mar. 3, 2017  (CN) .......................... 201710124819.2
Mar. 3, 2017  (CN) .......................... 201710126703.2

(51) Int. Cl.
*A61L 27/36* (2006.01)
*A61F 2/18* (2006.01)
(Continued)

(52) U.S. Cl.
CPC ............ *A61L 27/3633* (2013.01); *A61F 2/18* (2013.01); *A61L 27/3654* (2013.01);
(Continued)

(58) Field of Classification Search
None
See application file for complete search history.

(56) References Cited

U.S. PATENT DOCUMENTS 6,206,931 B1 * 3/2001 Cook ................. A61L 27/3839
523/113
2008/0213335 A1 * 9/2008 Cook .................... A61L 31/005
424/572
(Continued)

FOREIGN PATENT DOCUMENTS

AU  2009335032 A1 * 7/2010 ............. A61B 17/11
AU  2013323747 A1 * 3/2015 ............... A61F 2/12
(Continued)

OTHER PUBLICATIONS

A Comparative Study of Three Methods for Preparing Porcine Intestinal Submucosa Extracellular Matrix, China Academic Journal Electronic Publishing House (1994-2017).
(Continued)

*Primary Examiner* — Jennifer Dieterle
*Assistant Examiner* — Melissa A Hoban
(74) *Attorney, Agent, or Firm* — The Dobrusin Law Firm, PC (57) ABSTRACT

Disclosed are a biological tissue matrix material, a preparation method therefor and the use thereof in an otological repair material. The biological tissue matrix material com-
(Continued)

prises an extracellular matrix. The extracellular matrix comprises a collagen fiber, a growth factor and fibronectin. The biological tissue matrix material has a low amount of DNA residue, a low immunogenicity, a high anti-infection ability, and a strong repair capability.

11 Claims, 4 Drawing Sheets

(51) Int. Cl.
    *A61L 27/54*     (2006.01)
    *A61L 27/56*     (2006.01)
    *A61L 27/58*     (2006.01)

(52) U.S. Cl.
    CPC .......... *A61L 27/3691* (2013.01); *A61L 27/54* (2013.01); *A61L 27/56* (2013.01); *A61L 27/58* (2013.01); *A61F 2002/183* (2013.01); *A61L 2300/414* (2013.01); *A61L 2430/14* (2013.01); *A61L 2430/40* (2013.01)

(56) References Cited

U.S. PATENT DOCUMENTS

| | | | |
|---|---|---|---|
| 2008/0028268 A1 | 11/2008 | Johnson | |
| 2008/0286268 A1 | 11/2008 | Johnson | |
| 2010/0168689 A1* | 7/2010 | Swain | A61N 5/062 604/313 |
| 2014/0088701 A1* | 3/2014 | Sun | A61L 27/3695 623/23.72 |
| 2017/0035937 A1* | 2/2017 | Southard | A61L 27/3683 |

FOREIGN PATENT DOCUMENTS

| | | | | |
|---|---|---|---|---|
| CN | 101433735 A | | 5/2009 | |
| CN | 101563450 A | * | 10/2009 | ......... A61L 27/3633 |
| CN | 102256609 A | * | 11/2011 | ........... A61F 2/0059 |
| CN | 103157143 A | | 6/2013 | |
| CN | 104740685 A | | 7/2015 | |
| CN | 104971380 A | | 10/2015 | |
| CN | 105233343 A | | 1/2016 | |
| WO | 2007/03 0743 A3 | | 7/2007 | |
| WO | 2009/023276 | | 2/2009 | |
| WO | WO-2011062621 A2 | * | 5/2011 | ............ C12M 21/08 |
| WO | WO-2013086404 A1 | * | 6/2013 | ............... A61F 2/08 |

OTHER PUBLICATIONS

International Search Report dated Dec. 7, 2017, Application No. PCT/CN2017/080894.
Riccardo D' Eredita, Porcine small intestinal submucosa (SIS) myringoplasty in children: A randomized controlled study, pp. 1085-1089 (2015).
Qi Xing, Decelllularization of Fibroblast Cell Sheets for Natural Extracellular Matrix Scaffold Preparation, vol. 21 (2015).
A. Farag, Decellularized Periodontal Ligament Cell Sheets with Recellularization Potential, Research Reports, (2014).
Jing-Cong Luo, A multi-step method for preparation of porcine small intestinal submucosa (SIS), Biomaterials 32 (2011).
Thomas W. Gilbert, Decellularization of Tissues and Organs, Biomaterials 27, (2006).
A. Azhim, The use of sonication treatment to decellularize aortic tissues for preparation of bioscaffolds, Journal of Biomaterials Applications, (2014).

* cited by examiner

BIOLOGICAL TISSUE MATRIX MATERIAL, PREPARATION METHOD THEREFOR AND USE THEREOF IN OTOLOGICAL REPAIR MATERIAL

TECHNICAL FIELD

The present disclosure relates to the technical field of medical biological material, and in particular, relates to a biological tissue matrix material, a preparation method thereof and a use thereof, and further relates to an immunogen-removed biological tissue matrix material, a specific preparation method and the application thereof in otological repair materials.

BACKGROUND

The tympanic membrane, which is also referred to as eardrum, is an elliptical translucent membrane located at the junction of the tympanic cavity of middle ear and the external auditory canal, forms the lateral wall of the tympanic cavity, and separates the external auditory canal and the middle ear cavity. In the process of auditory conduction, the structure of the tympanic membrane enables the gain of the incoming sound wave, and the external sound is transmitted to the auditory nerve through the action on otosteon, thus enabling a living organism to obtain the perception to the external sound. Since the tympanic membrane itself is relatively fragile, due to the conditions such as infection, cholesteatoma, contact of a foreign object or large pressure difference between the inside and outside of the tympanic cavity in daily life, the eardrum may occur to perforation or even damage, and even the structure of the entire tympanic cavity may be damaged.

In the prior art, xenobiotic materials such as paper, egg membrane and gelatin sponge are adopted for repairing, or the autologous materials such as the mastoid periosteum, the temporal fascia and the venous valve are used for repairing. As for the xenobiotic materials, due to the poor biocompatibility thereof and the difficulty in absorption, a new problem will be brought about. Although the autologous material has no biocompatibility problem, since it needs to be collected from self-body, an additional surgery is required for the patient, which results in additional damage to the patient's body and brings additional pain to the patient. In addition, the nasopharynx and the middle ear are connected via the pharyngotympanic tube. Since the pharyngotympanic tube of a child is short, wide and straight and is in horizontal position, the pathogens and the secretions may easily enter the middle ear through the pharyngotympanic tube to cause acute inflammation, thus causing the perforation of the eardrum. Moreover, the thicknesses of these xenobiotic or allogenic materials are much larger than that of the tympanic membrane, which may influence the hearing recovery after the tympanic membrane is repaired. Furthermore, a surgery of carrying out the collection of autologous biological material on children will increase the difficulty of the surgery additionally.

Extracellular matrix (ECM) material which takes an animal tissue as a raw material based on the tissue engineering principles is a main development direction. ECM is a complex organic three-dimensional whole which is constructed by a variety of macromolecular substances such as collagen, non-collagen protein, aminoglycan and elastic protein according to a certain proportion and structure, provides a suitable place and microenvironment for the survival and activities of various cells, and is able to regulate the growth, shape, metabolism, migration, proliferation and differentiation of various cells and further regulate and control the functions of the tissues and the organs. One serious consequence of the tissue defect is the loss of "soil" (i.e., ECM), which is also the reason why the organism itself cannot realize tissue repair and regeneration. Natural ECM may be used as the "soil" for tissue regeneration and is an ideal tissue repair material. Removal of the cell components from the animal tissues may remove most of the immunogenicity and preserve the ECM components, so that an ideal biological repairing material may be developed. Currently, the biological active materials which have been used for clinical use comprise the ECM materials such as allogeneic dermis, porcine small intestinal submucosa, porcine dermis, and embryo bovine dermis. Among them, the decellularized small intestinal submucosa (SIS) matrix material is the most ideal tissue repair material recognized by the current academia.

On one hand, the animal-derived DNA residue is the main defect of the present ECM products. Studies have already proved that serous cyst is caused by the TH2 inflammatory cytokine reaction, and this reaction is caused by the chronic immune response of the animal-derived DNA. On the other hand, SIS material is treated with substances such as hydrogen peroxide, hypertonic salt(s) and alkali solution in the prior art, which is easy to damage the extracellular matrix of the SIS material, and thus affecting the quality of the product. In another aspect, the existing products (such as the Biodesign otological repair product of America Cook Biotech Incorporated) are only filled with a sheet-like material, and the shape of the material is not adjusted based on the shape of the ear canal to improve the climbing and adhering effect of the cells and facilitate the repair of the tympanic membrane, The present disclosure adopts a tympanic membrane repair material prepared by an animal-derived immunogen-removed small intestinal submucosa tissue material. On one hand, the occurrence of the aforementioned problems is avoided. Besides, the present disclosure also uses the small intestinal submucosa tissue material to prepare a supporting structure, therefore, both the chemical properties and the physical structure of the material are more conductive to the climbing and adhering of the cells and the repair of the tissue(s). The repair material may induce the growth of the patient's own cells, provide a template for the cells to reconstruct the damaged tissue and to repair it to a functionalized tissue or organ, and the immunogen-removed matrix is gradually degraded, which is basically synchronous with the regeneration process of the reconstructed tissue. Finally, the immunogen-removed matrix patch is completely replaced by the host tissue, so that the tympanic membrane is restored. This repair material does not cause an immunogenic reaction, and is easy to be processed into a required shape. Moreover, the patients do not need to suffer the pain of an additional surgery.

SUMMARY

The present disclosure provides a biological tissue matrix material, which improves the existing decellularization technology of the biological repair patches, so that the biological tissue matrix material of the present disclosure, as compared with the existing products, has a lower DNA residual amount, a lower immunogenicity, a higher anti-infection ability and a stronger repair capability.

The present disclosure provides an otological repair material, wherein the otological repair material may induce the growth of the patient's own cells, provide a template for the cells to reconstruct the damaged tissue and repair it to a functionalized tissue or organ, and the immunogen-removed matrix is gradually degraded, which is basically synchronous with the regeneration process of the reconstructed tissue, and finally, the immunogen-removed matrix patch is completely replaced by the host tissue.

The present disclosure provides a biological tissue matrix material, this material comprises an extracellular matrix, and the extracellular matrix comprises a collagen fiber, a growth factor and a fibronectin (FN).

The extracellular matrix (small intestinal submucosa matrix material) described in the present disclosure is made of the small intestinal submucosa tissue material (small intestinal submucosa).

The small intestinal submucosa tissue material described in the present disclosure is a mammalian small intestinal submucosa tissue material.

The small intestinal submucosa tissue material described in the present disclosure is a small intestinal submucosa tissue material of a porcine or a bovine.

The residual amount of the animal-derived DNA (the residual amount of DNA in the animal-derived biomaterial) in the extracellular matrix described in the present disclosure is less than 10 ng/mg, preferably, less than 3 ng/mg, and the clearance rate of alpha-Gal antigen is not lower than 99%. DNA and alpha-Gal are antigens, and if the content of these substances in the biological material is too high, they may cause immunological rejection in the human body after being put into the human body. The effective control of the aforementioned content overcomes the defect of the aforementioned immunological rejection, and the removal of the aforementioned substances is achieved by the decellularization step.

The technical solution provided by the the present disclosure is an otological repair material, wherein the repair material is made of the biological tissue matrix material, the repair material comprises a base layer and one or more convex portions arranged on the base layer.

The convex portion has a hemispherical shape, conical shape, rectangular shape, or circular truncated cone shape. The aforementioned structure may enhance the strength of the repair material, and is beneficial for filling the tympanic cavity and is beneficial for the climbing and adhering of the cells on the damaged tympanic membrane after being filled into the tympanic cavity.

The base layer is at least composed of a layered small intestinal submucosa matrix material which is subjected to drying treatment, and the convex portion is composed of the small intestinal submucosa matrix material which is subjected to crushing and drying treatment.

The growth factor components described in the present disclosure are the basic growth fibroblast factor (bFGF) and the vascular endothelial growth factor (VEGF).

The otological repair material described in the present disclosure has a porous structure at the micro level, and the porosity is 60% or more.

The tensile breaking strength of the otological repair material described in the present disclosure is greater than 50 N/cm.

The present disclosure also provides a preparation method of the aforementioned biological tissue matrix material, which comprises the following steps:

(1) initial treatment of the raw material: taking the small intestinal submucosa tissue material, washing and filtering to dryness;

(2) virus inactivation: soaking the small intestinal submucosa tissue material with a peroxyacetic acid-ethanol solution to carry out virus inactivation;

(3) washing the small intestinal submucosa tissue material obtained in step (2) under an ultrasonic environment, and then filtering to dryness;

(4) decellularization: treating the small intestinal submucosa tissue material with a decellularizing solution in the ultrasonic environment to carry out decellularization;

(5) carrying out washing in the ultrasonic environment to obtain the small intestinal submucosa matrix material.

In the peroxyacetic acid-ethanol solution of step (2) of the present disclosure, the volume percentage concentration of peroxyacetic acid is 0.1% to 5%, the volume percentage concentration of ethanol is 5% to 40% (formulated into a solution with water), and the volume ratio of the peroxyacetic acid-ethanol solution to the small intestinal submucosa tissue material is (3 to 20):1; the inactivation time is 2 to 4 hours, and the temperature range of the inactivation is 10 to 40° C.

In the washing process of step (3) of the present disclosure, the small intestinal submucosa tissue material is washed with a washing liquid, and the washing liquid is a PBS solution with a pH value of 7.2 to 7.4, the temperature of the PBS solution is 20° C., and the ratio (volume ratio) of the PBS solution to the small intestinal submucosa tissue material is (20 to 40):1; then, the purified water is used for washing, the ratio of the purified water to the small intestinal submucosa tissue material is (20 to 40):1, and the washing is stopped when the conductivity is detected as 10 82 S/cm or less; and the washing process is carried out in an ultrasonic washing machine, the frequency is preferably 40 kHz, and the power is preferably 3000 W or more.

The decellularizing solution of step (4) of the present disclosure comprises trypsin and a PBS solution, said decellularizing solution also comprises EDTA, EDTA-2Na, or EDTA-4Na; the mass percentage concentration of the trypsin in the decellularizing solution is 0.01% to 0.2%, preferably 0.02% to 0.05%; the concentration of EDTA, EDTA-2Na or EDTA-4Na is 0.1 to 1 mmol/L, preferably 0.4 to 0.8 mmol/L; the pH value of the decellularizing solution is 7.0 to 8.0, preferably 7.2 to 7.5; the volume ratio of said decellularizing solution to the small intestinal submucosa tissue material is (20 to 40):1, the decellularization process is carried out in a dual-frequency ultrasonic device, wherein the frequency range of the low frequency is 20 to 40 KHz, the frequency of the high frequency is 60 to 90 KHz, the low-frequency treatment lasts for 5 to 40 min, the high-frequency treatment lasts for 5 to 40 min, and the temperature range of the decellularizing solution is 20 to 35° C.; and the ultrasonic power is 5000 W or more. Trypsin and EDTA are used to destroy the connection between the cells and the extracellular matrix. The low-frequency ultrasound is used to crush the cells, meanwhile, the high-frequency ultrasound is used to act on the crushed cells and extracellular matrix, further enabling the cells to be separated from the extracellular matrix, so as to achieve the purpose of decellularization. By using the aforementioned manner, each step in the whole process of separating the cells from the matrix is strengthened, so that the cells are completely separated from the matrix. The optimal immunogen removal effect is achieved.

In the washing process of step (5) of the present disclosure, the small intestinal submucosa tissue material is washed with a washing liquid, and the washing liquid is a PBS solution with a pH value of 7.2 to 7.4, and the ratio (volume ratio) of the PBS solution to the small intestinal submucosa tissue material is (20 to 40):1; then, a cooled water for injection is used for washing, the ratio of the water for injection to the small intestinal submucosa tissue material is (20 to 40):1, the temperature of the water for injection is 20 to 35° C., and the washing is stopped when the difference of the conductivity between the water for injection after the washing and the water for injection before the washing is detected as 1 μS/cm or less. The washing process is carried out in the ultrasonic washing machine, the frequency is preferably 40 kHz, and the power is preferably 3000 W or more.

Based on the aforementioned preparation method of the biological tissue matrix material, the preparation method of the otological repair material of the present disclosure further comprises the following steps:

(6) preparation of a slurry of the small intestinal submucosa matrix material: using a low-temperature crushing device to crush the small intestinal submucosa matrix material treated by step (5), adding an acetic acid solution into the crushed matrix material to form the slurry of the small intestinal submucosa matrix material;

(7) drying: fixing an immunogen-removed small intestinal submucosa matrix material treated by step (5) on a first forming mold, and then subjecting the mold to drying in a heat circulating oven; and (8) lyophilization: using a second forming mold with one or more pits, filling the slurry of the small intestinal submucosa matrix material treated by step (6) into the pits, and scarping the slurry to smooth; and then, laying the dried and immunogen-removed small intestinal submucosa matrix material obtained in step (7) flat on the slurry scraped to smooth in the second forming mold, and placing the second forming mold in a vacuum lyophilizer to carry out lyophilization.

The preparation of the slurry of the small intestinal submucosa matrix material in step (6) of the present disclosure comprises using the low-temperature crushing device to crush the crushed small intestinal submucosa matrix material obtained in step (5) and adding an acetic acid solution into the crushed matrix material to form the slurry of the small intestinal submucosa matrix material, wherein the mass percentage concentration of the acetic acid solution is 0.1% to 0.8%, preferably 0.2% to 0.3%, and the mass ratio of the small intestinal submucosa matrix material to the acetic acid solution is 1:25 to 1:500, preferably 1:50 to 1:100.

The first forming mold in said step (7) comprises a base plate with needles, a cover plate and a pressing block, and the specific structural diagram may be referred to the Chinese Invention Patents CN20131020358.6 and CN201310203602.2. One or more layers of the small intestinal submucosa matrix material are laid flat on the base plate with needles and covered with the cover plate, and a pressing block of 5 to 10 kg is pressed against the cover plate, so that the material is flat, the water overflows from around, and the upper and lower layers of the material are in close contact.

In step (8), the pit of the second forming mold may be a hemisphere, a circular truncated cone, a cone, a cylinder, a prism, a pyramid, or a prismoid; or the pit may be an irregular block adapted to the shape of the tympanic cavity. The slurry of the small intestinal submucosa matrix material obtained in step (6) is filled into one or more pits in the second forming mold and is scraped to smooth, so that the surfaces of the slurry in all pits (exposed to the upper surfaces of the open sides of the pits) are basically on the same plane. The small intestinal submucosa matrix material obtained in step (7) is covered on said plane and is in contact with said slurry, preferably, a pressing block of 5 to 10 kg is placed on said small intestinal submucosa matrix material to provide a close contact. In the lyophilization step, the second forming mold with the slurry is pre-frozen to −45° C. and the temperature is kept for 1 to 2 hours, the temperature is then adjusted to −15° C. and kept for 5 to 7 hours, the temperature is then adjusted to 0° C. and kept for 1 to 4 hours, and finally, the temperature is adjusted to 25° C. and kept for 2 to 6 hours.

In step (8), the diameter of the pit is 0.1 to 20 mm, for example, 0.5 to 2 mm, 4 to 8 mm, or 12 to 18 mm.

The aforementioned preparation method of the present disclosure also comprises step (9) of punching and packaging and step (10) of sterilization analysis.

Said punching and packaging in step (9) is specifically as follows. The dried material is cut into a fixed shape (including a square shape, a circular shape or other shapes) on the mold, and then put into a mechanical punching machine. The holes are punched at an interval of 0.9 cm and the diameter of the holes is 1.5 mm, and then the Tyvek packaging bag is used for packaging Said sterilization analysis in step (10) is specifically as follows. Ethylene oxide is used to carry out sterilization, and the sterilization conditions are as follows. First, the temperature is kept at 20 to 40° C. for 2 to 4 hours, the humidity is 30% to 70%, then ethylene oxide with a concentration of 300 to 1000 mg/L is introduced therein, and the sterilization is carried out for 4 to 8 hours. The analysis process is carried out in a ventilated analysis chamber, the temperature is controlled between 10 to 30° C., and the analysis process lasts for 14 to 28 days The present disclosure uses the porcine small intestinal submucosa material as a raw material.

The using standard of the water for injection in the present disclosure is in accordance with the provisions in the Chinese Pharmacopoeia.

In the use of the biological tissue matrix material of the present disclosure in the preparation of the medical repair material, said medical repair material is used for repairing tissue defects in otology, face, periosteum, nerve, endocranium, dura mater spinalis, tendon, ligament, urinary tract, bladder, ureter, inguinal hernia, esophageal hiatus hernia, ventral hernia, breast, or uterine mucosa. More specifically, it is used to repair various tissue defects in otology, periosteum, nerve, endocranium, dura mater spinalis, tendon, ligament, urinary tract, bladder, ureter, inguinal hernia, esophageal hiatus hernia, ventral hernia, breast, uterine mucosa, and the like, as well as the protection, isolation, fixation, repair, reconstruction and reinforcement of various tissues, including but not limited to the protection, isolation, fixation, repair, reconstruction, and reinforcement of a wound surface after a soft tissue injury such as tumor removal, surgical resection, the reinforcement of an anastomotic stoma, and the like, The present disclosure further uses the biological tissue matrix material for otological repair.

Compared with the prior art, the present disclosure has the following significant advantages and beneficial effects.

(1) Multi-frequency ultrasonic decellularization process: According to the response of the porcine small intestinal submucosa material to different ultrasonic frequencies, the multi-frequency ultrasound is used to treat the porcine small intestinal submucosa, the using amount and the action time of the chemical reagent during the cell elution process are reduced, and the integrity of the collagen fiber in the extracellular matrix and the three-dimensional porous structure are protected after the ultrasonic decellularization process.

(2) Enzymatic cell elution process: A complex solution of trypsin and EDTA is used, the decellularization process is mild, the damage to the matrix structure is reduced, and the active growth factor in the matrix is preserved.

(3) Multi-frequency ultrasound is combined with the enzymatic cell elution process to increase the efficiency of the decellularization process.

(4) Molding process technology: By the molding method and the vacuum lyophilization, the binding strength between the multi-layers of matrix is improved, the risk of the occurrence of serous cyst after implantation is reduced, the design of the porous structure is considered as well, and the porosity may reach 90% or more, which is beneficial to the vascularization and the tissue reconstruction after implantation. A twice forming tool is used to obtain a small intestinal submucosa matrix material with a convex structure on one side, this convex structure is capable of playing a role in supporting during the damage of the tympanic membrane and the repairing process of the tympanic cavity, and having a buffering and protecting effect during the repair process of perforation. A double-layer composite structure having a fixed layer and a porous layer is formed by a method of combining drying with lyophilization. The porosity of the porous layer is large, which is beneficial to the growth of cells and is able to increase the repair speed of the tissue. Since this convex structure has a small density and a high porosity, the in vivo decomposition time is not affected.

(5) Sterilization process: The in vivo degradation process of the product is adjusted by the sterilization process, so that the decellularized biological repair patch is gradually degraded, which is basically synchronous with the regeneration process of the reconstructed tissue, and finally, the decellularized biological repair patch is completely replaced by the host tissue.

(7) Hydrogen peroxide is used for disinfection in the prior art, however, hydrogen peroxide has a strong oxidizability, which may damage the extracellular matrix of the material. The present disclosure overcomes the aforementioned defect by using a peroxyacetic acid-ethanol solution to carry out virus inactivation. In addition, in the prior art, only hypertonic salt(s) and alkali solution are used to carry out the decellularizing treatment, however, the effects of these two reagents are too strong, and the extracellular matrix may be easily damaged. The present disclosure uses a milder complex solution of trypsin and EDTA together with the dual-frequency ultrasonic treatment to carry out the decellularization treatment, this step is a very important step in the manufacture of the biological material, only when the content of the cells acting as the immunogen is reduced to extremely low or completely removed, the material implanted into the body will not induce an immune reaction, thus ensuring the safety of the material. The connection between the cells and the extracellular matrix is destroyed by using trypsin and EDTA, the low-frequency ultrasound is then used to crush the cells, meanwhile, the high-frequency ultrasound is used to act on the crushed cells and extracellular matrix, and the cells are further separated from the extracellular matrix to achieve the aim of decellularization. As for each step of decellularization, the corresponding methods are used for the detailed treatment, so that the decellularization effect is better and the residue of the cells is less.

(8) The biological tissue matrix material prepared by the preparation method of the biological tissue matrix material of the present disclosure is a kind of platform product. This matrix material has a porous structure at the micro level, which is a stent provided for cell growth. Depending on the different locations of the tissue(s) and organ(s) where the matrix material is placed, the functional cells of each tissue and organ climb and grow on the matrix material to form the corresponding tissue structure and exert the corresponding tissue function, and the matrix material becomes a part of the tissue. Therefore, the product prepared according to the present disclosure may faun a variety of medical products aiming at a variety of indications. These products may be applied to various tissue defects, including but not limited to the tissue defects in otology, periosteum, nerve, endocranium, dura mater spinalis, tendon, ligament, urinary tract, bladder, ureter, inguinal hernia, esophageal hiatus hernia, ventral hernia, breast, and uterine mucosa, as well as the protection, isolation, fixation, repair, reconstruction and reinforcement of various tissues, including but not limited to the protection, isolation, fixation, repair, reconstruction, and reinforcement of a wound surface after a soft tissue injury such as tumor removal, surgical resection, the reinforcement of an anastomotic stoma, and the like. Among them, the otological repair patch is a specific application of this biological tissue matrix material.

DETAILED DESCRIPTION

The present disclosure will be further described specifically with reference to the following examples, however, the embodiments of the disclosure are not limited thereto.

It must be noted that as used herein and in the appended claims, the singular forms "a", "an", and "the" include plural referents unless the context clearly dictates otherwise.

EXAMPLE 1

This example related to a preparation method of an animal-derived implantable biological repair patch, which comprised the following steps.

(1) Initial Treatment of the Raw Material

A porcine small intestinal submucosa tissue material (porcine SIS) was taken and divided into a specified size with a width of 8 cm and a length of 15 cm. The useless tissues (such as the lymphoid tissue) were removed, washed with tap water for 1 to 3 times, and then washed with the purified water until there was no stain on the surface. The washed porcine small intestinal submucosa tissue material was placed in a water filtering device such as a filter screen for more than 5 minutes, and the water was drained. When the small intestine was taken and used, the small intestine after the filtration of water was measured by a device for measuring the volume such as a measuring cylinder.

(2) Virus Inactivation

The porcine small intestinal submucosa tissue material was soaked with a peroxyacetic acid-ethanol solution to carry out virus inactivation, and this process could be carried out in a stainless steel barrel. In the peroxyacetic acid-ethanol solution, the concentration of peroxyacetic acid was 1% (volume percentage), the concentration of ethanol was 24% (volume percentage), and the ratio (volume ratio) of the peroxyacetic acid-ethanol solution to the porcine small intestinal submucosa tissue material was 5:1, the inactivation time was 2 hours, the inactivation temperature (namely, the temperature of the peroxyacetic acid-ethanol solution in which the porcine small intestinal submucosa tissue material was soaked) was 20° C.

(3) Washing Process

The porcine small intestinal submucosa tissue material was washed with a washing liquid, the washing liquid was a PBS solution with a pH value of 7.2 to 7.4, the temperature of the PBS solution was 20° C., and the ratio (volume ratio) of the PBS solution to the porcine small intestinal submucosa tissue material was 30:1. Preferably, the washing was carried out for 3 times, and lasted for 20 minutes each time. Then, the purified water was used for washing, the ratio of the purified water to the porcine small intestinal submucosa tissue material was 30:1, and the washing was stopped when the conductivity was detected as 10 μS/cm or less. The washing process was carried out in an ultrasonic washing machine, the frequency was preferably 40 kHz, and the power was preferably 3000 W or more.

(4) Decellularization

The decellularizing solution was a PBS solution comprising trypsin with a mass percentage concentration of 0.025% and EDTA-2Na with a concentration of 0.5 mmol/L. The pH value of the decellularizing solution was 7.2 to 7.4. The mixing ratio (volume ratio) of the decellularizing solution to the porcine small intestinal submucosa tissue material was 30:1. The decellularizing process was carried out in the dual-frequency ultrasonic device, including two frequencies, i.e., a low frequency and a high frequency, wherein the frequency of the low frequency was 20 KHz, the frequency of the high frequency was 80 KHz, the ultrasonic power was 5 KW, the low-frequency treatment lasted for 10 min, the high-frequency treatment lasted for 10 min, the temperature was 30° C., and the ultrasonic power was 5000 W.

(5) Washing Process

The washing liquid was used for carrying out washing, the washing process was carried out in the ultrasonic washing machine, and the power of the ultrasonic wave was 3000 W or more. The washing liquid was the PBS solution with a pH of 7.2 to 7.4, the temperature of the PBS solution was 20° C., and the ratio (volume ratio) of the PBS solution to the porcine small intestinal submucosa tissue material was 30:1. Preferably, the washing was carried out 3 times, and lasted for 20 minutes each time. Then, a cooled water for injection at a temperature of 20° C. was used for washing, the ratio (volume ratio) of the water for injection to the porcine small intestinal submucosa tissue material was 30:1, the washing was stopped when the difference of the conductivity between the water for injection after the washing and the water for injection before the washing was detected as 1 μS/cm or less, the frequency was preferably 40 kHz, and the power was preferably 3000 W or more.

EXAMPLE 2

This example related to a preparation method of an animal-derived implantable biological repair patch, which comprised the following steps.

(1) Initial Treatment of the Raw Material:

The porcine small intestinal submucosa tissue material was taken and divided into a specified size with a width of 8 cm and a length of 15 cm. The useless tissues (such as the lymphoid tissue) were removed, and washed with the purified water until there was no stain on the surface. The washed porcine small intestinal submucosa tissue material was placed in a water filtering device such as a filter screen for more than 5 minutes, and the water was drained. When the small intestine was taken and used, the small intestine after the filtration of water was measured by a device for measuring the volume such as a measuring cylinder.

(2) Virus Inactivation

The porcine small intestinal submucosa tissue material was soaked with a peroxyacetic acid-ethanol solution to carry out virus inactivation, and this process could be carried out in a stainless steel barrel. In the peroxyacetic acid-ethanol solution, the concentration of peroxyacetic acid was 4% (volume percentage), the concentration of ethanol was 30% (volume percentage), the ratio (volume ratio) of the peroxyacetic acid-ethanol solution to the porcine small intestinal submucosa tissue material was 10:1, the inactivation time was 2 hours, and the temperature was 22° C.

(3) Washing Process

The porcine small intestinal submucosa tissue material was washed with a washing liquid, the washing liquid was a PBS solution with a pH value of 7.2 to 7.4, the temperature of the PBS solution was 22° C., and the ratio (volume ratio) of the PBS solution to the porcine small intestinal submucosa tissue material was 25:1. The washing was carried out 3 times, and lasted for 20 minutes each time. Then, a water for injection at a temperature of 20° C. was used for washing, the ratio of the water for injection to the porcine small intestinal submucosa tissue material was 30:1, the washing was stopped when the conductivity was detected as 10 μS/cm or less. The washing process was carried out in the ultrasonic washing machine.

(4) Decellularization

The decellularizing solution was a PBS solution comprising trypsin with a mass percentage concentration of 0.1% and EDTA-2Na with a concentration of 0.5 mmol/L. The pH value of the decellularizing solution was 7.2 to 7.4. The mixing ratio (volume ratio) of the decellularizing solution to the porcine small intestinal submucosa tissue material was 30:1.

The decellularizing process was carried out in the dual-frequency ultrasonic device, including two frequencies, i.e., a low frequency and a high frequency, wherein the frequency of the low frequency was 25 KHz, the frequency of the high frequency was 70 KHz, the ultrasonic power was 5 KW, the low-frequency treatment lasted for 7 min, and the high-frequency treatment lasted for 15 min, the temperature was 30° C., and the ultrasonic power was 5200 W.

(5) Washing Process

The washing liquid was used for washing, and the washing process was carried out in the ultrasonic washing machine, the power of the ultrasonic wave was 3000 W or less. The washing liquid was a PBS solution with a pH value of 7.2 to 7.4, the temperature of the PBS solution was 20° C., and the ratio (volume ratio) of the PBS solution to the porcine small intestinal submucosa tissue material was 30:1. Preferably, the washing was carried out 3 times, and lasted for 20 minutes each time. Then, a water for injection at a temperature of 20° C. was used for washing, the ratio (volume ratio) of the water for injection to the porcine small intestinal submucosa tissue material was 30:1, and the washing was stopped when the difference of the conductivity between the water for injection after the washing and the water for injection before the washing was detected as 1 µS/cm or less.

EXAMPLE 3

The manufacturing method involved in the present disclosure could also comprise the following steps.

(6) Fixing and Molding

Fixing and molding was carried out on the mold, said mold comprised a base plate with needles and a pressing frame, and different molds needed to be selected according to different specifications and sizes. The porcine small intestinal submucosa matrix material prepared in step (5) was laid flat on the base plate with needles, the pressing frame was placed on the porcine small intestinal submucosa matrix material, the size of the pressing frame could be the final cut size or wider, and the base plate with needles and the pressing frame were fixed (7) Vacuum Lyophilization Vacuum lyophilization was carried out in a vacuum lyophilizer, and the lyophilization process of the product needed to be reconfined according to different equipments. The mold was laid flat in the vacuum lyophilizer, the door of the lyophilizing chamber was closed, the circulation pump was turned on for about 1 minute, and the compressor was turned on to cool the lyophilizing box. The mold of step (6) together with the above porcine small intestinal submucosa matrix material were pre-frozen to −45° C. and the temperature was kept for 1 to 2 hours, then the vacuum pump was turned on, the temperature was adjusted to −15° C. and kept for 5 to 7 hours, the temperature was then adjusted to 0° C. and kept for 2 hours, finally, the temperature was adjusted to 25° C. and kept for 4 hours, and the vacuum lyophilization was completed. The pressure intensity in the chamber of the lyophilizing device was 20 to 25 Pa.

Steps (6) and (7) could be arbitrarily combined with the preceding examples.

EXAMPLE 4

(1) Pretreatment of the tissue: The porcine small intestinal submucosa tissue material was taken and divided, and the lymphoid tissue was removed. The porcine small intestinal submucosa tissue material was washed with tap water, and then washed with the purified water until there was no stain on the surface. The washed porcine small intestinal submucosa tissue material was placed in a water filtering device such as a filter screen for more than 5 minutes, and the water was drained.

(2) Virus inactivation: The porcine small intestinal submucosa tissue material was soaked with a peroxyacetic acid-ethanol solution, and this process could be carried out in a stainless steel barrel. The concentration (volume percentage) of peroxyacetic acid was 0.6%, the concentration (volume percentage) of ethanol was 7%, the inactivation time was 2 hours, the ratio (volume ratio) of the solution to the porcine small intestinal submucosa tissue material was 9:1, and the temperature was 20° C.

(3) Washing process: First, ultrasonic treatment was carried out with a PBS solution with a pH value of 7 in the ultrasonic washing machine after the virus inactivation was completed, the volume ratio of the PBS solution to the small intestinal submucosa tissue material was 20:1. The small intestinal submucosa tissue material was then washed with the purified water for several times, the washing was stopped when the conductivity of the washing liquid was detected as 10 µS/cm or less, and the volume ratio of the purified water to the small intestinal submucosa tissue material was 20:1.

(4) Immunogen removal: A PBS solution with a pH of 7 comprising trypsin with a concentration (mass percentage) of 0.1% and EDTA with a concentration of 0.5 mmol/L was used, and the mixture was ultrasonically oscillated. The ultrasound comprised at least two frequencies, wherein the low frequency was 25 KHz, the high frequency was 75 KHz, the low-frequency treatment lasted for 15 min, the high-frequency treatment lasted for 8 min, the temperature range was 20 to 35° C., and the ratio (volume ratio) of the solution to the porcine small intestinal submucosa tissue material was 30:1, the whole process needed to be carried out in a multi-frequency ultrasonic device, and the ultrasonic power was at least 5000 W. The multi-frequency ultrasound comprised at least two frequencies, wherein the low frequency was 18 KHz, the high frequency was 80 KHz, the low-frequency treatment lasted for 15 min, the high-frequency treatment lasted for 8 min, and the temperature range was 20 to 35° C.

(5) The washing process comprised the following steps. The ultrasonic treatment was carried out with a PBS solution with a pH of 7.2 to 7.5, the volume ratio of the solution to the small intestinal submucosa tissue material was 30:1, the washing lasted for 30 minutes each time and was carried out 2 to 4 times, and the detected pH was between 6 and 8. The cooled water for injection was used for washing, the ratio of the water for injection to the small intestinal submucosa tissue material was 30:1, and the washing was stopped when the difference of the conductivity of the water for injection before and after the washing was detected as 1 µS/cm or less. The washing process could be carried out in the ultrasonic washing machine, the frequency was 40 kHz, the power was 3000 W, and the porcine small intestinal submucosa matrix material was obtained.

(6) Preparation of the Slurry of the Small Intestinal Submucosa Matrix

The small intestinal submucosa matrix material obtained in step (5) was crushed by a low-temperature crushing device. The low-temperature crushing device is a liquid nitrogen freezing and crushing device, the liquid nitrogen and the small intestinal submucosa material were transferred into the liquid nitrogen freezing and crushing device, the small intestinal submucosa material was frozen by the liquid nitrogen, and a high-speed rotary cutter head of the crushing device was used to carry out crushing. An acetic acid solution was added into the crushed matrix material to form the slurry of the small intestinal submucosa matrix material, wherein the mass percentage concentration of the acetic acid solution was 0.3%, and the mass ratio of the small intestinal submucosa matrix material to the acetic acid solution was 1:60.

(7) Drying: This process was carried out in a heat circulating oven, preferably an oven that had a cleanliness of class 100. The first forming mold was composed of three parts: a base plate with needles, a cover plate, and a pressing block. One or more layers of the porcine small intestinal submucosa matrix material was laid flat on the base plate with needles, covered with the cover plate, and a pressing block of 5 to 10 kg was pressed against the cover plate, so that the material was flat, the water overflowed from around, and the upper and the lower layers of the material were in close contact. Then, it was placed in the oven. The blower of the oven was turned on, pre-heated to 40° C. and the temperature was kept for about 16 hours.

(8) Lyophilization: The second forming mold was used, wherein the second forming mold had hemispherical pits, the hemispherical pits had a diameter of 1 mm. The slurry was placed on the surface of the second forming mold, so that the slurry was filled into the pits of the second forming mold, and then the slurry was scraped to smooth to allow the surfaces of the slurry in all pits to be basically on the same plane. The small intestinal submucosa matrix material obtained in step (7) was covered on the plane and was in contact with the slurry. Also, a pressing block of 5 to 10 kg was placed on the small intestinal submucosa matrix material, so that the small intestinal submucosa material which was dried by step (7) was in close contact with the slurry. The mold together with the matrix material thereon were placed in a vacuum lyophilizer, the door of the lyophilizing chamber was closed, the circulation pump was turned on for about 1 min, and then the compressor was turned on to cool the lyophilizing box. The product was pre-frozen to −45° C. and the temperature was kept for 2 hours, the vacuum pump was turned on, and the temperature of the product was adjusted to about −15° C. for sublimation. After about 6 hours, the temperature of the product was adjusted to 0° C. and kept for 2 hours, and the temperature of the product was adjusted to 25° C. and kept for 4 hours.

EXAMPLE 5

The manufacturing method involved in the present disclosure could also comprise the following steps.

(9) Punching and Packaging

After the dried material was taken out, it was cut by a cutting device on the mold, and then placed into a mechanical punching machine to carry out punching. Then, a double-layer Tyvek packaging bag was used for packaging. Sterile transportation and operation were required in this process.

(10) Sterilization Analysis

Ethylene oxide was used for sterilization, and the sterilization conditions were as follows. First, the temperature was kept at 40° C. for 4 hours, the humidity was 30% to 70%, ethylene oxide with a concentration of 300 to 1000 mg/L was then introduced therein, and the sterilization was carried out for 6 hours. The analysis process was carried out in a ventilated analysis chamber, the temperature was controlled at 20° C., and the process lasted for 14 days.

Steps (9) and (10) could be arbitrarily combined with the aforementioned examples.

Figure 1:
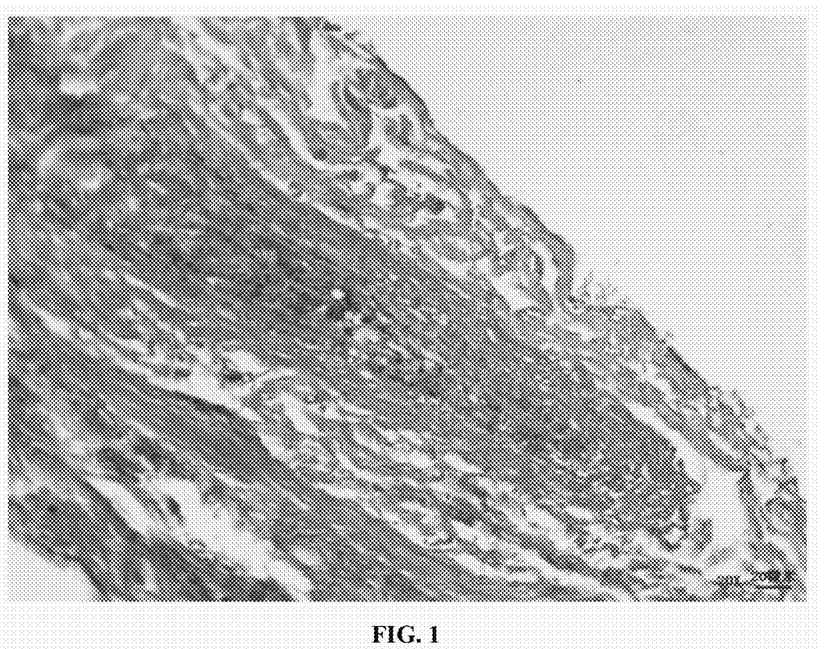
FIG. 1 shows an HE staining diagram of the decellularized matrix material of the present disclosure.
Figure 2:
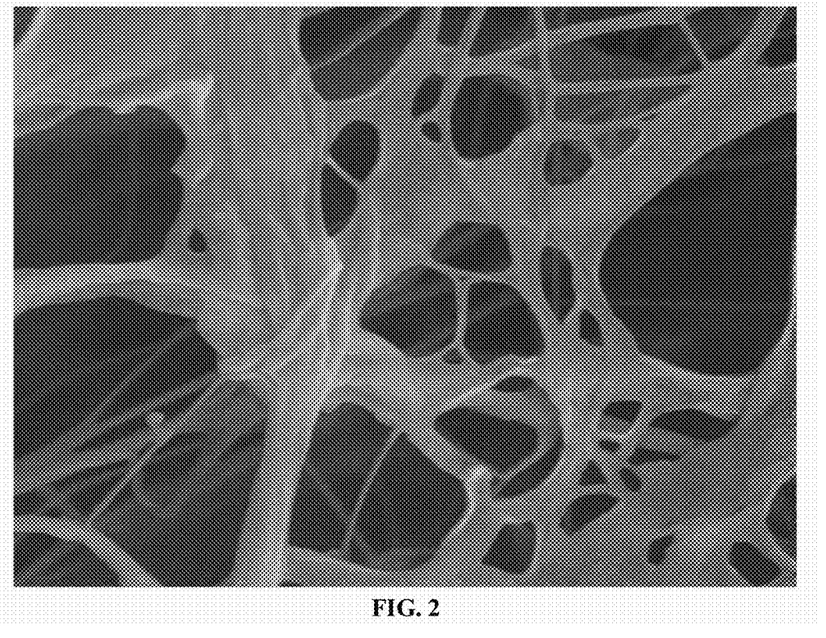
FIG. 2 shows a diagram of the ultrastructure of the lyophilized biological repair patch prepared in the present disclosure.
Figure 3:
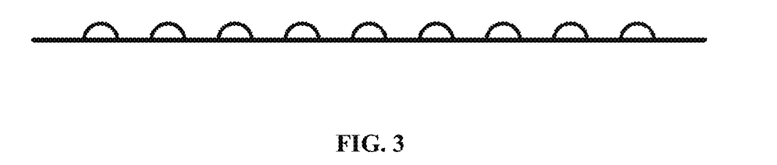
FIG. 3 shows a schematic side view of an otological repair material according to an embodiment of the present disclosure.
Figure 4:
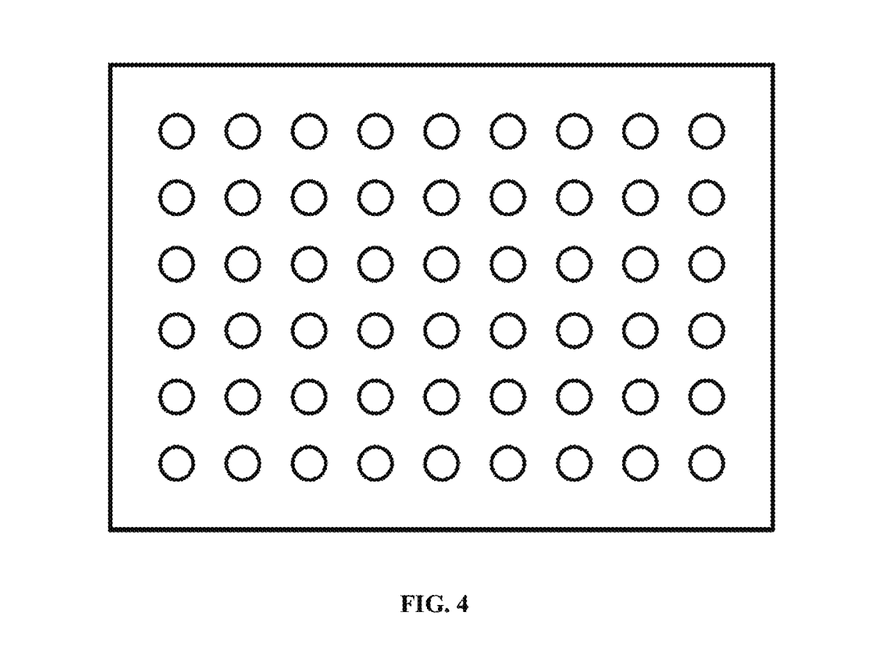
FIG. 4 shows a schematic plan view of an otological repair material according to an embodiment of the present disclosure.
Figure 5:
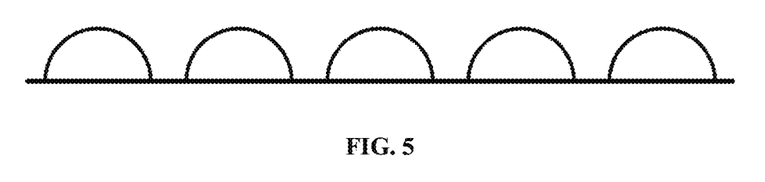
FIG. 5 shows a schematic side view of an otological repair material according to another embodiment of the present disclosure.
Figure 6:
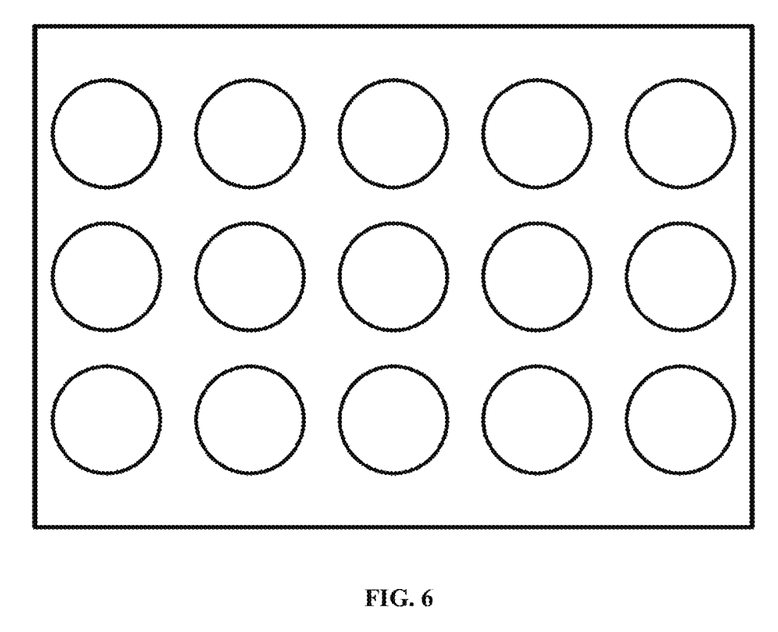
FIG. 6 shows a schematic plan view of an otological repair material according to another embodiment of the present disclosure.
Figure 7:
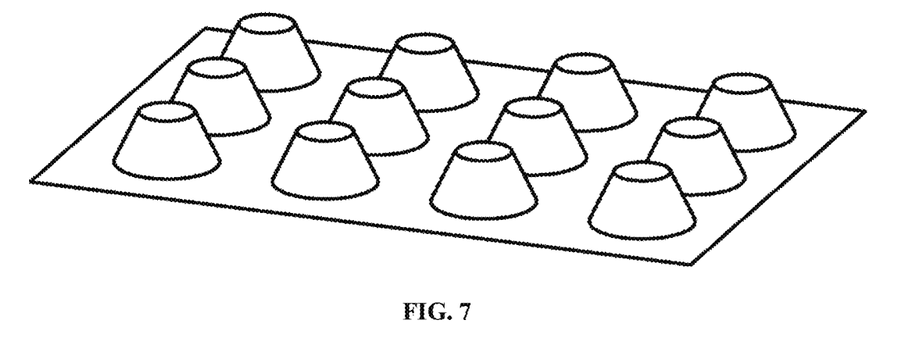
FIG. 7 shows a schematic diagram of an otological repair material according to another embodiment of the present disclosure.
Figure 8:
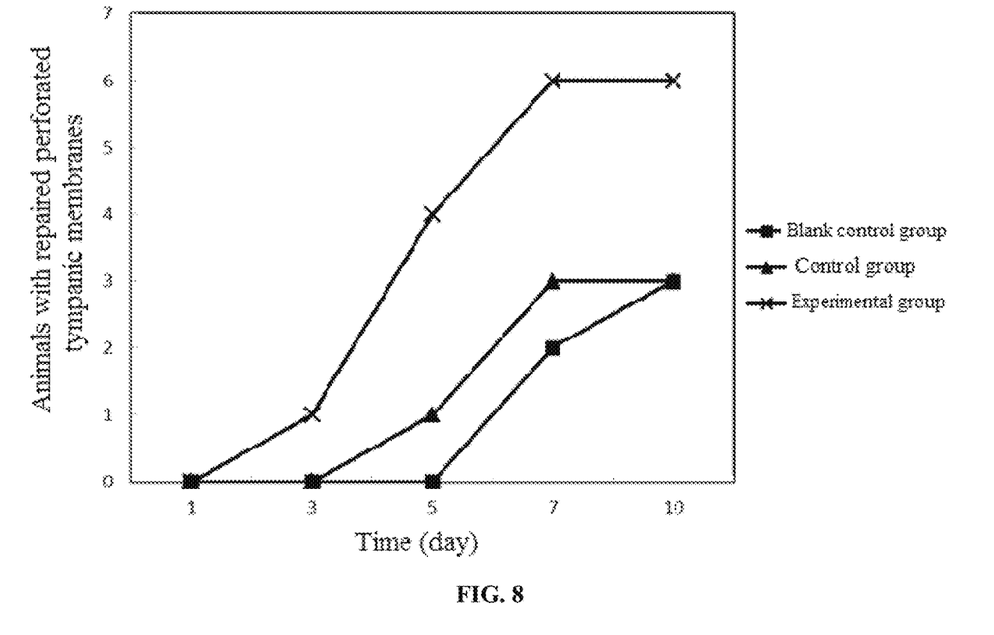
FIG. 8 shows a diagram of the animal experimental data according to an embodiment of the present disclosure.

As could be seen from FIG. 1 and FIG. 2, in the sample obtained by the preparation process of the present disclosure, the immunogens such as cells were completely removed, and the extracellular matrix portion was intact, smooth, and free of damage. Therefore, the biological matrix material obtained by using the preparation process of the present disclosure maintained the porous space structure of the small intestinal submucosa material, allowed the small intestinal submucosa material to have a good mechanical strength, and basically eliminated the immunogenicity at the same time.

The biological repair patch materials prepared by the above-mentioned examples were subjected to the examination of physical and chemical properties and biological detection.

1) DNA residue: According to the method for detecting the residual DNA in a biological preparation in the fourth part of the Chinese Pharmacopoeia, 2015 edition, the fluorescent staining method was used to detect the residual amount of DNA in the sample provided by Example 1. Result: the residual amount of DNA in the sample provided by Example 1 was less than 3.64±0.96 ng/mg.

2) Clearance rate of galactosidase (alpha-Gal): 2 mg of the animal-derived biological material which was a Gal-positive reference substance and 2 mg of Gal antigen-negative reference substance were taken, respectively. 1 ml of lysis solution was added and the lysis lasted for 30 to 90 min, and samples with 20, 10, 5, 2,5, 1.25 and 0.625 μg of Gal which were used for a Gal standard curve were prepared. 50 mg of the test sample before and after the immunogen removal were taken, respectively. 2 ml of lysis solution was added and the lysis lasted for 30 to 90 min. The supernatant obtained after the reaction of the lysis solution with M86 antibody was taken and added into a 96-well plate, a secondary antibody was added, and a color developing agent was added. The ELISA method was used to detect the absorbance value at 450 nm, and the Gal value of the sample was calculated according to the standard curve. The Gal value of the material before the immunogen removal treatment was $17.79\pm1.89\times10^{14}$/mg, the Gal value of the sample in Example 1 was $0.13\pm0.01\times10^{14}$/mg, and the clearance rate of galactosidase (alpha-Gal) was 99.27% or more.

3) Virus detection: The pseudorabies virus was selected as an indicator virus, the DNA copy number was detected by using the real-time quantitative PCR method, and three batches of samples were detected. Result: the copy number of the virus DNA was 0.

4) Bacterial endotoxin: The detection was carried out according to GB/T 14233.2-2005 "Methods for Testing Infusion, Transfusion and Injection Equipments for Medical Use, Part 2: Biological Test Methods", and three batches of samples in total were detected. Result: the bacterial endotoxin was less than 20 EU/package.

5) Identification of collagen subtypes: Immunohistochemical staining method was used to detect Types I, III, IV and VI collagens. The sample was sliced to a thickness of 3 μm continuously, and the slices were dewaxed by xylene and dehydrated by gradient ethanol. The slices were transferred into a water bath in a rice cooker (containing 0.01 mol/L of trisodium citrate buffer solution at pH 6.0), the temperature was kept at 95 to 100° C., the slices were boiled for 20 min to carry out the restoration of antigen, and then the slices were taken out and naturally cooled at room temperature. The slices were washed with a phosphate buffer solution (PBS) for 5 min×3 times. Two-step immunohistochemical method: The monoclonal antibodies as the primary antibodies of Types I, III, IV and VI collagens were respectively added dropwise, the concentrations were 1:100. The mixture was incubated at 4° C. in a refrigerator overnight and then incubated at room temperature for 60 min, and washed three times with PBS. The Envision reaction solution was added dropwise and incubated at room temperature for 30 min. The mixture was washed three times with PBS, and was developed with 0.05% of 3,3-diaminobenzidine and 0.03% of $H_2O_2$ for 5 to 10 min. The running water was used for washing, and hematoxylin was used for staining. The slices were dehydrated by ethanol with an incremental gradient, made transparent with xylene, and sealed by the conventional resin. The results showed that the brownish yellow staining was found in all the four stained specimens under a microscope, the results of which were positive, indicating that Types I, III, IV and VI collagens could be detected in the samples.

6) Detection of the content of the polysaccharide substances: 10 samples were taken and extracted, a Biocolor chondroitin sulfate assay kit was used to detect the content of chondroitin sulfate, and the average value of the content of chondroitin sulfate in the samples was 5236±185 µg/g. A hyaluronic acid assay kit was used to detect the content of hyaluronic acid (HA), and the result showed that the average value of the retention amount of hyaluronic acid (HA) in the samples was 296±23 µg/g.

7) Identification of the types of the active factors: After the sample was soaked in PBS for 24 hours, it was fixed in 4% paraformaldehyde for 5 to 10 min, washed with 0.1 mol/L of PBS for 3 times, 5 min for each time, and then transferred onto a glass slice coated with polylysine via a glass tubule to carry out the immunohistochemical staining. The titers of the LN antibody, FN antibody and integrin were all 1:100, 0.5% trypsin was used for digestion for 3 to 5 min to expose the antigen, and 0.1% Triton X100 acted for 10 min to increase the penetrability of the antibody. The result of the immunohistochemical staining was positive, and the surface sample contained substances such as fibronectin, laminin, integrin and the ligands thereof.

8) Residual amount of the growth factors: As for the sample of Example 1, the ELISA method was used to detect the contents of the basic fibroblast growth factor (bFGF) and the vascular endothelial growth factor (VEGF) in the sample, and the animal tissue before the immunogen removal was used as control. The result showed that the contents of the basic fibroblast growth factor (bFGF) before and after the immunogen removal were respectively 2155±189 ng/L and 828±90 ng/L, 35% or more of the growth factor was retained, the contents of the vascular endothelial growth factor (VEGF) before and after the immunogen removal were respectively 633±51 ng/L and 249±16 ng/L, and 35% or more of the growth factor was retained.

9) Tensile strength: A sample was prepared according to Example 1. The sample was cut into a size of 2×5 cm, subjected to test immediately after being placed under a condition in which the relative humidity was 40% to 60% and the temperature was 22° C.±2° C. for 2 hours. The two ends of the sample were fixed on the chuck of a tensile testing machine, and were sequentially stretched outward at a speed of 100 mm/min until the sample was broken.

The longitudinal sample and the transverse sample were tested respectively. The final measurement results showed that the longitudinal tensile strength could reach 30 N, and the transverse tensile strength could reach 15 N.

10) Residual amount of ethylene oxide: The test was carried out according to the method specified in Item 9 of GB/T14233.1-2008 "Methods for Testing Infusion, Transfusion and Injection Equipments for Medical Use, Part 1: Chemical Analytical Methods". Result: the residual amount of ethylene oxide in the product was no more than 10 µg/package.

11) Heavy metal inspection: Lead and chromium were tested according to the method specified in Item 5.9.1 of GB/T 14233.1-2008 "Methods for Testing Infusion, Transfusion and Injection Equipments for Medical Use, Part 1: Chemical Analytical Methods", mercury and arsenic were tested according to the method specified in Item 5.9.3 of GB/T 14233.1-2008 "Methods for Testing Infusion, Transfusion and Injection Equipments for Medical Use, Part 1; Chemical Analytical Methods", the total heavy metal content of the lead, chromium, mercury and arsenic in the product inspection solution was less than 1 µg/g.

EXAMPLE 6

Biocompatibility tests were carried out on the sample of Example 1, the detection items comprised pyrogen, cytotoxicity, delayed-type hypersensitive reaction, intradermal reaction, acute systemic toxicity, Ames test, mouse lymphoma cell mutation test, chromosome aberration, implantation, and subchronic toxicity.

1) Pyrogen

According to a ratio of 1:5 (the mass ratio of the sample to the extraction medium), the sample was extracted at 37±1° C. for 72±2 hr to prepare a test solution, and the extraction medium was physiological saline. The test was carried out according to the method specified in GB/T 14233.2-2005, and the product had no pyrogen reaction.

2) Cytotoxicity

According to a ratio of 1:5 (the mass ratio of the sample to the extraction medium), the sample was extracted at 37±1° C. for 24±2 hr to prepare a test solution, and the extraction medium was a serum-containing MEM culture medium. The test solution was taken and subjected to the test according to the method specified in GB/T16886.5-2003, and the result showed that the cytotoxic reaction of the product was not higher than grade 1.

3) Delayed-Type Hypersensitive Reaction

According to a ratio of 1:5 (the mass ratio of the sample to the extraction medium), the sample was extracted at 37±1° C. for 72±2 hr to prepare a test solution, and the extraction media were physiological saline and cottonseed oil. The test was carried out according to the test method specified in GB/T 16886.10-2005 Part 10: Test Methods for Irritation and Delayed-type Hypersensitive Reaction. Result: the product had no delayed-type hypersensitive reaction.

4) Intradermal Reaction

According to a ratio of 1:5 (the mass ratio of the sample to the extraction medium), the sample was extracted at 37±1° C. for 72±2 hr to prepare a test solution, and the extraction media were physiological saline and cottonseed oil. The test was carried out according to the test method specified in GB/T 16886.10-2005 Part 10: Test Methods for Irritation and Delayed-type Hypersensitive Reaction. Result: the difference between the average score of the test sample and the solvent control was less than 1.0.

5) Acute Systemic Toxicity

According to a ratio of 1:5 (the mass ratio of the sample to the extraction medium), the sample was extracted at 37±1° C. for 72±2 hr to prepare a test solution, and the extraction media were physiological saline and cottonseed oil. The test solution was taken and subjected to the test according to the test method specified in GB/T16886.11-2011. Result: the product had no acute systemic toxic reaction.

6) Ames Test

According to a ratio of 1:5 (the mass ratio of the sample to the extraction medium), the sample was extracted at 37±1° C. for 72±2 hr to prepare a test solution, and the extraction media were physiological saline and DMSO. The test was carried out according to the method specified in GB/T16886.3-2008. The result of the Ames test of the product was negative.

7) Mouse Lymphoma Cell Mutation Test

According to a ratio of 1:5 (the mass ratio of the sample to the extraction medium), the sample was extracted at 37±1° C. for 72±2 hr to prepare a test solution, and the extraction media were physiological saline and DMSO. The test was carried out according to the method specified in GB/T16886.3-2008. The result of the mouse lymphoma cell mutation test of the product was negative.

8) Chromosome Aberration Test

According to a ratio of 1:5 (the mass ratio of the sample to the extraction medium), the sample was extracted at 37±1° C. for 72±2 hr to prepare a test solution, and the extraction media were physiological saline and DMSO. The test was carried out according to the method specified in GB/T16886.3-2008. The result of the chromosome aberration test of the product was negative.

9) Implantation

The implantation was carried out according to the method specified in GB/T16886.6-1997. Results: 1 week after the muscle implantation, the infiltration of neutrophils, lymphocytes and macrophages were visible around the sample, and no cystic cavity was formed; 4 weeks after the muscle implantation, a small amount of macrophages and lymphocytes were visible around the sample, the collagen fibers and fibroblasts proliferated, and a fiber cystic cavity was formed; and 12 weeks after the muscle implantation, a small amount of lymphocytes were visible around the sample, and the collagen fibers and the fiber cystic cavity were compact and regular.

10) Subchronic Toxicity

This test was carried out according to the method specified in GB/T168811. Result: there was no subchronic toxic reaction.

EXAMPLE 7

Animal Experiment:

Animal experimental model, 60 Wistar rats were used as the experimental animal models. All the animals were intraperitoneal anesthetized with sodium pentobarbital (0.3 ml/100 g), and a circular perforation of about 1.5 mm×1.5 mm at the tense part was made in the lower quadrant of the back of the bilateral tympanic membranes of the rat by a scorching needle tip under an electric auriscope. After the surgery, the intramuscular injection of ampicillin (150 mg/kg) was used to prevent infection, once a day for 5 consecutive days. The otological repair material was used to prepare the biological tympanic membrane repair patch. 60 rats were randomly divided into two groups. As for the 30 rats in the first group, the left ear was the blank control group, and the right ear was treated with the biological tympanic membrane repair patch. In the second group, the sterile dry cotton balls were placed in the external auditory canal of the left ear, and the right ear was treated with the biological tympanic membrane repair patch. At 1, 3, 5, 7, and 10 days after the surgery, 6 rats were sacrificed in each group, the temporal bone was anatomized, the lateral wall of the otocyst was peeled off, the intact tympanic membrane was taken out, and the repair condition of the tympanic membrane was observed. The obtained tympanic membrane specimens were fixed with 10% formaldehyde, embedded in paraffin, sectioned, and stained by the conventional HE staining, and the two-step immunohistochemical method was used for detection. The immunohistochemical results were tested by the paired-sample t test (compared with the same rat), and $P<0.05$ indicated that the difference had statistical significance. The results showed that under a light microscope, the epithelial cells thickened after the biological tympanic membrane repair patch was used for 3 days, the cells changed from flat cells to polygonal cells, the distance between the cells increased, the nuclear to cytoplasmic ratio increased, the epithelial layer was separated from the fibrous layer, and the epithelial proliferation was obvious. At day 5, most of the fibrous layers of the tympanic membrane thickened, and the columnar epithelium of the inner layer also proliferated. At day 7, the tympanic membrane was basically healed, and the structure was close to that of the normal tympanic membrane. At day 10, complete repair of the tympanic membrane perforation was observed in only 3 rats (6 rats in total) of the blank control group and the control group. As for the immunohistochemical image analysis, as compared with the blank control group and the group using the sterile dry cotton balls, the difference of the expression values of TGF-alpha and bFGF between the group using the biological tympanic membrane repair patch and the above-mentioned two groups had statistical significance, and $p<0.05$. Therefore, the biological tympanic membrane repair patch could improve the expression of TGF-alpha and bFGF during the healing of the tympanic membrane perforation, prolong the expression time thereof, shorten the healing time of the perforated tympanic membrane, promote the healing of the perforation, and enable the healed tissue to be closer to the structure of the normal tympanic membrane tissue.

In conclusion, the present disclosure related to an immunogen-removed matrix as an otological repair material, wherein (1) DNA residue was able to reach 10 ng/mg or less, which was 30 to 50 ng/mg lower than the similar products, and the removal rate of galactosidase was high and was able to reach 99%;

(2) in the immunogen removal process, by controlling the ultrasonic power for the product, the effect of breaking cells and DNA could be achieved under the condition of a high power, and the substances within the broken cells could be effectively washed away under the condition of a low power;

(3) the mechanical strength was stronger, which was able to enable the otological repair material to have better mechanical properties and the degradation time was able to be controlled effectively, so that the otological repair material could match with the regeneration process of the human tissue after being implanted into the body; and (4) the method combining drying and lyophilization was used to form a two-layer composite structure having a fixed layer and a porous layer, and the porosity of the loose layer was large, which was beneficial for the growth of cells and was able to improve the repair speed of the tissue.

The aforementioned examples of the present disclosure are intended to be illustrative of the present disclosure and are not intended to limit the present disclosure, and any change within the meaning and the scope equivalent to those of the claims of the disclosure should be considered to be included within the scope of the claims.

What is claimed is:

1. A preparation method of a biological tissue matrix material, wherein the preparation method comprises the following steps:
   (1) initial treatment of a raw material: taking a small intestinal submucosa tissue material, washing, and filtering to dryness;
   (2) virus inactivation: soaking the small intestinal submucosa tissue material with a peroxyacetic acid-ethanol solution to carry out virus inactivation;

(3) washing the small intestinal submucosa tissue material obtained in step (2) under an ultrasonic environment, and then filtering to dryness;

(4) decellularization, wherein a decellularizing solution comprises trypsin and a PBS solution, the decellularizing solution also comprises EDTA, EDTA-2Na, or EDTA-4Na, and the small intestinal submucosa tissue material obtained in step (3) is treated with the decellularizing solution in a multi-frequency ultrasonic environment to carry out decellularization; and (5) washing a decellularized small intestinal submucosa tissue material obtained in step (4) under the ultrasonic environment to obtain a decellularized small intestinal submucosa matrix material; wherein in the peroxyacetic acid-ethanol solution in step (2), peroxyacetic acid has a volume percentage concentration of 0.1% to 5%, ethanol has a volume percentage concentration of 5% to 40%, a volume ratio of the peroxyacetic acid-ethanol solution to the small intestinal submucosa tissue material is (5 to 20):1, an inactivation time is 2 to 4 hours and a temperature range is 10 to 40° C.;

the trypsin in the decellularizing solution of step (4) has a mass percentace concentration of 0.01% to 0.2%, EDTA, EDTA-2Na or EDTA-4NA a has a concentration of 0.1 to 1 mmol/L, and the decellularizing solution has a pH value of 7.0 to 8.0; a volume ratio of the decellularizing solution to the small in intestinal submucosa tissue material is (20 to 40):1, a decellularization process is carried out in a dual-frequency ultrasonic device, in which a low frequency has a frequency range of 20 to 40 KHz, a low-frequency treatment lasts for 5 to 40 min, a high frequency has a frequency of 60 to 90 KHz, a high-frequency treatment lasts for 5 to 40 min the decellularizing solution has a temperature range of 20 to 35° C., and an ultrasonic power is 5000 W or more.

2. The preparation method of the biological tissue matrix material according to claim 1, wherein the mass percentage concentration of the trypsin in the decellularizing solution of step (4) is 0.02% to 0.05%, the concentration of EDTA, EDTA-2Na or EDTA-4Na is 0.4 to 0.8 mmol/L, and the pH value of the decellularizing solution is 7.2 to 7.5.

3. The preparation method of the biological tissue matrix material according to claim 2, wherein the preparation method also comprises the following steps:

(6) fixing and molding: placing one or more layers of the small intestinal submucosa matrix material obtained in step (5) on a mold; and (7) vacuum lyophilization: carrying out the lyophilization of the small intestinal submucosa matrix material in a vacuum lyophilizer.

4. A preparation method of an otological repair material, wherein the preparation method comprises steps (1) to (5) of the preparation method of the biological tissue matrix material according to claim 2, and also comprises the following steps:

(6) preparation of a slurry of the small intestinal submucosa matrix material: using a low-temperature crushing device to crush the small intestinal submucosa matrix material treated by step (5), and adding an acetic acid solution into the crushed matrix material to form the slurry of the small intestinal submucosa matrix material;

(7) drying: fixing an immunogen-removed small intestinal submucosa matrix material treated by step (5) on a first forming mold, and then subjecting the mold to drying in a heat circulating oven; and (8) lyophilization: using a second forming mold with one or more pits, filling the slurry of the small intestinal submucosa matrix material treated by step (6) into the pits and scraping the slurry to smooth, then laying the dried and immunogen-removed small intestinal submucosa matrix material obtained in step (7) flat on the slurry scraped to smooth in the second forming mold, and placing the second forming mold in a vacuum lyophilizer to carry out lyophilization.

5. The preparation method of the biological tissue matrix material according to claim 4, wherein the preparation method also comprises the following steps:

(9) punching and packaging, and (10) sterilization analysis;

wherein the punching and packaging in step (9) specifically comprises: cutting the small intestinal submucosa matrix material after being subjected to the vacuum lyophilization in step (7) into a fixed shape on the mold, then placing the small intestinal submucosa matrix material into a mechanical punching machine for punching, and then using a Tyvek packaging bag for packaging;

the sterilization analysis in step (10) specifically comprises: using ethylene oxide to perform sterilization, wherein a sterilization condition is that the temperature is first kept at 20 to 40° C. for 2 to 4 hours, a humidity is 30% to 70%, then ethylene oxide with a concentration of 300 to 1000 mg/L is introduced therein, and the sterilization is carried out for 4 to 8 hours; and carrying out an analysis process in a ventilated analysis chamber, controlling the temperature between 10 to 30° C., and lasting for 14 to 28 days.

6. The preparation method of the biological tissue matrix material according to claim 1, wherein the preparation method also comprises the following steps:

(6) fixing and molding: placing one or more layers of the small intestinal submucosa matrix material obtained in step (5) on a mold; and (7) vacuum lyophilization: carrying out the lyophilization of the small intestinal submucosa matrix material in a vacuum lyophilizer.

7. The preparation method of the biological tissue matrix material according to claim 6, wherein the fixing and molding in step (6) specifically comprises: a mold comprising a base plate with needles and a pressing frame, laying one or more layers of the small intestinal submucosa matrix material flat on the base plate with needles, placing the pressing frame on the small intestinal submucosa matrix material, and fixing the base plate with needles and the pressing frame;

the vacuum lyophilization in step (7) specifically comprises: placing a mold with the small intestinal submucosa matrix material in the vacuum lyophilizer; first, pre-freezing to −45° C., and keeping the temperature for 1 to 2 hours, then turning on a vacuum pump, adjusting the temperature to −15° C. and keeping the temperature for 5 to 7 hours, then adjusting the temperature to 0° C. and keeping the temperature for 2 hours, and finally, adjusting the temperature to 25° C. and keeping the temperature for 4 hours; and completing the vacuum lyophilization under a condition wherein a pressure intensity in a chamber of a lyophilization device is 1 to 50 Pa.

8. The preparation method of the biological tissue matrix material according to claim 6, wherein the preparation method also comprises the following steps:
- (9) punching and packaging, and
- (10) sterilization analysis;
- wherein the punching and packaging in step (9) specifically comprises: cutting the small intestinal submucosa matrix material after being subjected to the vacuum lyophilization in step (7) into a fixed shape on the mold, then placing the small intestinal submucosa matrix material into a mechanical punching machine for punching, and then using a Tyvek packaging bag for packaging;
- the sterilization analysis in step (10) specifically comprises: using ethylene oxide to perform sterilization, wherein a sterilization condition is that the temperature is first kept at 20 to 40° C. for 2 to 4 hours, a humidity is 30% to 70%, then ethylene oxide with a concentration of 300 to 1000 mg/L is introduced therein, and the sterilization is carried out for 4 to 8 hours; and carrying out an analysis process in a ventilated analysis chamber, controlling the temperature between 10 to 30° C., and lasting for 14 to 28 days.

9. A preparation method of an otological repair material, wherein the preparation method comprises steps (1) to (5) of the preparation method of the biological tissue matrix material according to claim 1, and also comprises the following steps:
- (6) preparation of a slurry of the small intestinal submucosa matrix material: using a low-temperature crushing device to crush the small intestinal submucosa matrix material treated by step (5), and adding an acetic acid solution into the crushed matrix material to form the slurry of the small intestinal submucosa matrix material;
- (7) drying: fixing an immunogen-removed small intestinal submucosa matrix material treated by step (5) on a first forming mold, and then subjecting the mold to drying in a heat circulating oven; and
- (8) lyophilization: using a second forming mold with one or more pits, filling the slurry of the small intestinal submucosa matrix material treated by step (6) into the pits and scraping the slurry to smooth, then laying the dried and immunogen-removed small intestinal submucosa matrix material obtained in step (7) flat on the slurry scraped to smooth in the second forming mold, and placing the second forming mold in a vacuum lyophilizer to carry out lyophilization.

10. The preparation method according to claim 9, wherein the preparation method also comprises the following steps:
- (9) punching and packaging; and
- (10) sterilization analysis;
- wherein the punching and packaging in step (9) specifically comprises: cutting the small intestinal submucosa matrix material after being subjected to the vacuum lyophilization in step (7) into a fixed shape on a mold, then placing the small intestinal submucosa matrix material into a mechanical punching machine for punching, and then using a Tyvek packaging bag for packaging;
- the sterilization analysis step in step (10) specifically comprises: using ethylene oxide to perform sterilization, wherein a sterilization condition is that the temperature is first kept at 20 to 40° C. for 2 to 4 hours, a humidity is 30% to 70%, then ethylene oxide with a concentration of 300 to 1000 mg/L is introduced therein, and the sterilization is carried out for 4 to 8 hours; and carrying out an analysis process in a ventilated analysis chamber, controlling the temperature between 10 to 30° C., and lasting for 14 to 28 days.

11. The preparation method of the biological tissue matrix material according to claim 1, wherein the preparation method also comprises the following steps:
- (6) fixing and molding: placing one or more layers of the small intestinal submucosa matrix material obtained in step (5) on a mold; and
- (7) vacuum lyophilization: carrying out the lyophilization of the small intestinal submucosa matrix material in a vacuum lyophilizer.

* * * * *